United States Patent [19]

Scherer

[11] Patent Number: 4,989,287
[45] Date of Patent: Feb. 5, 1991

[54] ELECTRIC TOOTHBRUSHES

[75] Inventor: Benjamin Scherer, Zürich, Switzerland

[73] Assignee: Gimelli & Co. AG, Zollikofen, Switzerland

[21] Appl. No.: 395,533

[22] Filed: Aug. 18, 1989

[30] Foreign Application Priority Data

Sep. 9, 1988 [DE] Fed. Rep. of Germany ....... 3830649
Feb. 8, 1989 [EP] European Pat. Off. ........... 89102098

[51] Int. Cl.⁵ ............................................. A46B 13/02
[52] U.S. Cl. ......................................... 15/22.1; 15/28; 433/131; 74/99
[58] Field of Search ................. 15/22 A, 22 R, 23, 28, 15/167 R, 29; 433/118, 122, 131, 134, 115; 74/50, 55, 99 R, 104, 107, 88, 89, 20

[56] References Cited

U.S. PATENT DOCUMENTS

| 2,215,031 | 9/1940 | Elmore | 15/28 |
| 3,160,902 | 12/1964 | Aymar | 15/22 R |
| 3,193,864 | 7/1965 | McKowsky | 15/167.1 |
| 3,478,433 | 11/1969 | Richmond | 433/134 |
| 4,156,620 | 5/1979 | Clemens | 134/6 |
| 4,432,729 | 2/1984 | Fattaleh | 433/118 |
| 4,827,550 | 5/1989 | Graham et al. | 15/22 R |
| 4,845,795 | 7/1989 | Crawford et al. | 15/28 |

FOREIGN PATENT DOCUMENTS 3406112 8/1985 Fed. Rep. of Germany .
3630499 3/1988 Fed. Rep. of Germany .
1525112 1/1967 France .

Primary Examiner—Philip R. Coe
Assistant Examiner—Gary K. Graham
Attorney, Agent, or Firm—Wegner, Cantor, Mueller & Player

[57] ABSTRACT

An electric toothbrush has a reciprocating connecting rod in a brush member. The brush member is constructed as a brush head at its front end and has there two rows of rotatable bristle holders which each engage with a cam in a transversely running groove in the connecting rod. Rectilinear movement of the connecting rod leads to an alternating rotating movement of the bristle holders.

17 Claims, 6 Drawing Sheets

4,989,287

ELECTRIC TOOTHBRUSHES

BACKGROUND OF THE INVENTION

The invention relates to an electric toothbrush with a handle which is to be manually guided and comprises a motor and gearing, and with a brush member which has a brush head with several cylindrical bristle holders rotating separately next to one another. Such a toothbrush is disclosed, for example, in U.S. Pat. No. 4,156,620.

In this known toothbrush, the brush member is not movable. The teeth are cleaned exclusively by the rotating movement of the bristle holders.

In the toothbrush known from U.S. Pat. No. 4,156,620 there is a connecting rod which is constructed as a toothed rack in the region of the brush head. The bristle holders each carry a gearwheel inside the brush head, all gearwheels in a row of bristle holders intermeshing and each second gearwheel in a row engaging in teeth in the toothed rack. Therefore, the adjacent bristle holders rotate in opposite directions when the connecting rod moves to and fro, and this is advantageous for cleaning teeth.

The known toothbrush is relatively complicated in construction owing to the plurality of gearwheels and the connecting rod constructed as a toothed rack. To prevent the gearwheels from jamming, the toothbrush must be produced with very close production tolerances. This entails high production costs and is accompanied by the risk of even slight inaccuracies in production leading to an interruption in operation.

SUMMARY OF THE INVENTION

The object of the invention is to improve a toothbrush of the type mentioned at the outset such that it can clean the teeth more vigorously and, at the same time, is able to massage the gums.

According to the invention, this object is achieved by providing an electric toothbrush having a handle, which is adapted to be manually guided and comprises a motor and gearing, and a brush member which has a brush head with a plurality of cylindrical bristle holders rotating separately next to one another, said gearing being constructed and arranged to set the brush holder into both an oscillating and a reciprocating movement.

Toothbrushes whose bristle members perform both an oscillating and a reciprocating movement are known, for example from FR-PS 1525112. However, the invention consists in transferring this principle of a rocking bristle member to a toothbrush with rotating tufts of bristles. This allows particularly effective cleaning of the teeth and, in addition, very good massage of the gums.

Another object of the invention is to provide a toothbrush of the type mentioned at the outset which is constructed such that the individual bristle holders can be driven by the simplest means so that the toothbrush can be produced economically and can operate particularly reliably. In order to achieve this object, a connecting rod is provided which has, inside the brush head, grooves running transversely to its main extension, into which the bristle holders each engage with a cam running parallel to their axis of rotation.

With such a toothbrush, gearwheels are not required for producing the rotating movement of the bristle holders. The rotating movement of the bristle holders is produced simply in that the connecting rod shifts the cam due to its reciprocating movement. The drive is therefore very simple in design and does not require close production tolerances. The term "transversely to the main extension" does not mean that the grooves have to run perpendicularly to the main extension; a course directed obliquely to it is sufficient. Instead of grooves, obliquely running projections are equivalent solutions.

The connecting rod must have inclined planes for rotating the cams.

In a particularly advantageous embodiment of the invention, the brush head has two adjacent rows of bristle holders and, in the central position of the connecting rod, the cams of the bristle holders in the two rows are orientated such that they face one another in the transverse direction to the brush member. As the cams face one another, the connecting rod can be narrow in construction in the region of the brush head, and the respective adjacent bristle holder in a row rotates in the opposite direction. If the cam were arranged alternately to the centre of the brush head and to the exterior of the brush head, then all bristle holders would rotate in the same direction. The invention therefore allows the direction of rotation of the bristle holders to be altered in a simple manner.

With electric toothbrushes which are constructed like a manual toothbrush with respect to the brush head, it has proved advantageous if the brush head makes a circling movement. This circling movement is produced by a special gear which pushes a toothbrush shaft to and fro and also allows it to oscillate about its longitudinal axis. Reference is made to U.S. Pat. No. 3,160,902 as an example of such a state of the art. This known principle of the oscillation of the toothbrush head can easily be transferred to the toothbrush according to the invention if the connecting rod is arranged non-rotatably in the brush member and the brush member is arranged on the handle so as to rotate about its longitudinal axis and if the gearing is designed to rotate the connecting rod alternately about its longitudinal axis in addition to shifting the connecting rod in the longitudinal direction.

The brush member can be produced inexpensively and can easily be exchanged if, according to a further embodiment of the invention, the brush member is detachably connected to the handle and the connecting rod has a snap connection at its handle end for connection to the shaft of the toothbrush.

Instead of allowing the entire brush member to oscillate about its longitudinal axis, the individual bristle holders can also travel alternately more or less far from the brush member if, according to a further embodiment of the invention, the connecting rod is rotatable about its longitudinal axis in the brush member and the brush member on the handle is arranged non-rotatably about its longitudinal axis and if the bristle holders are arranged axially movably with respect to their axis of rotation in the brush head.

Particularly simple gearing for producing the rotating movement and oscillating movement is distinguished in that it comprises a bevel wheel which is driven by a bevel pinion of the motor, revolves about a pivot pin running transversely to the connecting rod and, with an eccentric peg orientated parallel to its pivot pin, engages in a recess in a rocker fixed on a toothbrush shaft which is axially movably and rotatably arranged in the handle and is orientated in the longitudinal direction of the handle part.

The gearing operates quite particularly with low friction and can be produced very inexpensively if, according to a further embodiment of the invention, a sliding block inserted in a recess in the rocker is arranged rotatably on the eccentric peg and if the two lateral faces of the sliding block running parallel to the axis of the toothbrush shaft and/or the corresponding lateral faces of the recess are bent or bevelled to allow a rocking motion of the rocker.

The rocking motion of the rocker is produced particularly simply if, according to a further embodiment of the invention, the part of the rocker comprising the recess for the sliding block is at a radial distance from the toothbrush shaft. With this embodiment, the sliding block acts at a considerable distance from the pivot axis of the rocker which is at the same time the axis of the toothbrush, on the rocker. A relatively great rocking moment is thus produced so that the oscillating movement of the brush member takes place with sufficiently great force.

An embodiment in which the eccentric peg engages from the side of the toothbrush into the sliding block is very compact.

The invention allows numerous embodiments. One embodiment is shown in the drawings and is described below for further clarification of its basic principle.

DESCRIPTION OF PREFERRED EMBODIMENT

Figure 1:
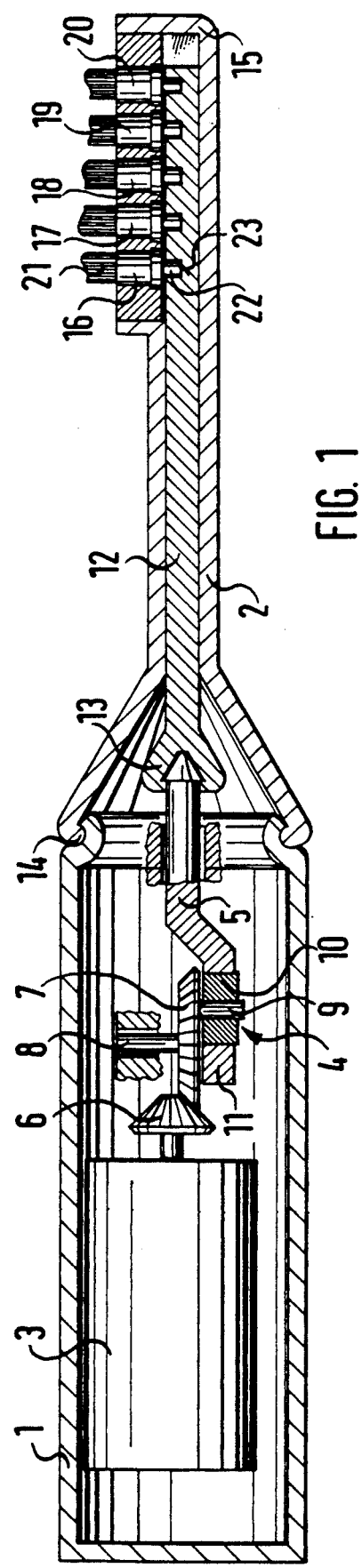
FIG. 1 shows a schematic longitudinal section through a toothbrush according to the invention.

The toothbrush shown as a whole in FIG. 1 consists of a handle 1 and a brush member 2 fixed detachably and rotatably thereon. In the handle 1 there is arranged a motor 3 which drives a toothbrush shaft 5 via gearing 4 such that the toothbrush shaft 5 simultaneously performs an oscillating movement about its longitudinal axis and an axial shifting movement. The gearing 4 has a bevel pinion 6 which is driven by the motor 3 and drives a bevel wheel 7 which is rotatable about a pivot pin 8 arranged transversely to the motor 3. Parallel to its pivot pin 8, this bevel wheel 7 has an eccentric peg 9 on which there rests in rotatable manner a sliding block 10 arranged non-rotatably inside a rocker 11. Owing to the circular path of movement of the eccentric peg 9, the rocker 11 is moved forwards and backwards. It cannot move to the side as the rocker 11 is rigidly connected to the toothbrush shaft 5 and the toothbrush shaft 5 is held axially movably and rotatably in the handle 1. This guidance of the toothbrush shaft 5 causes the rocker 11 with the toothbrush shaft 5 to rock about the longitudinal axis of the toothbrush shaft 5 when the eccentric peg moves from the plane of the drawing, as illustrated in more detail below.

A connecting rod 12 is arranged axially movably but non-rotatably relative to the brush member 2 in the brush member 2. This connecting rod 12 has, at its handle end, a snap connection 13 with which it is locked to the toothbrush shaft 5 non-rotatably relative to the toothbrush shaft 5. The brush member 2 is accordingly detachably connected to the handle with a catch connection 14. However, this catch connection 14 is constructed such that the brush member 2 can rotate about its longitudinal axis relative to the handle 1, this being necessary as the toothbrush shaft 5 and therefore also the connecting rod 12 can rotate to a limited extent about the longitudinal axis of the toothbrush.

The brush member 2 has, at its front end, a brush head 15 into which there are rotatably inserted several cylindrical bristle holders 16 to 20 which project with tufts 21 of bristles from the brush head 15. Inside the brush head, the bristle holders 16 to 20 each have a cam 22 which engages in a transversely running groove 23 of the connecting rod 12. When the connecting rod 12 moves to and fro, the cams 23 are shifted and the bristle holders 16 to 20 are thus rotated.

Figure 2:
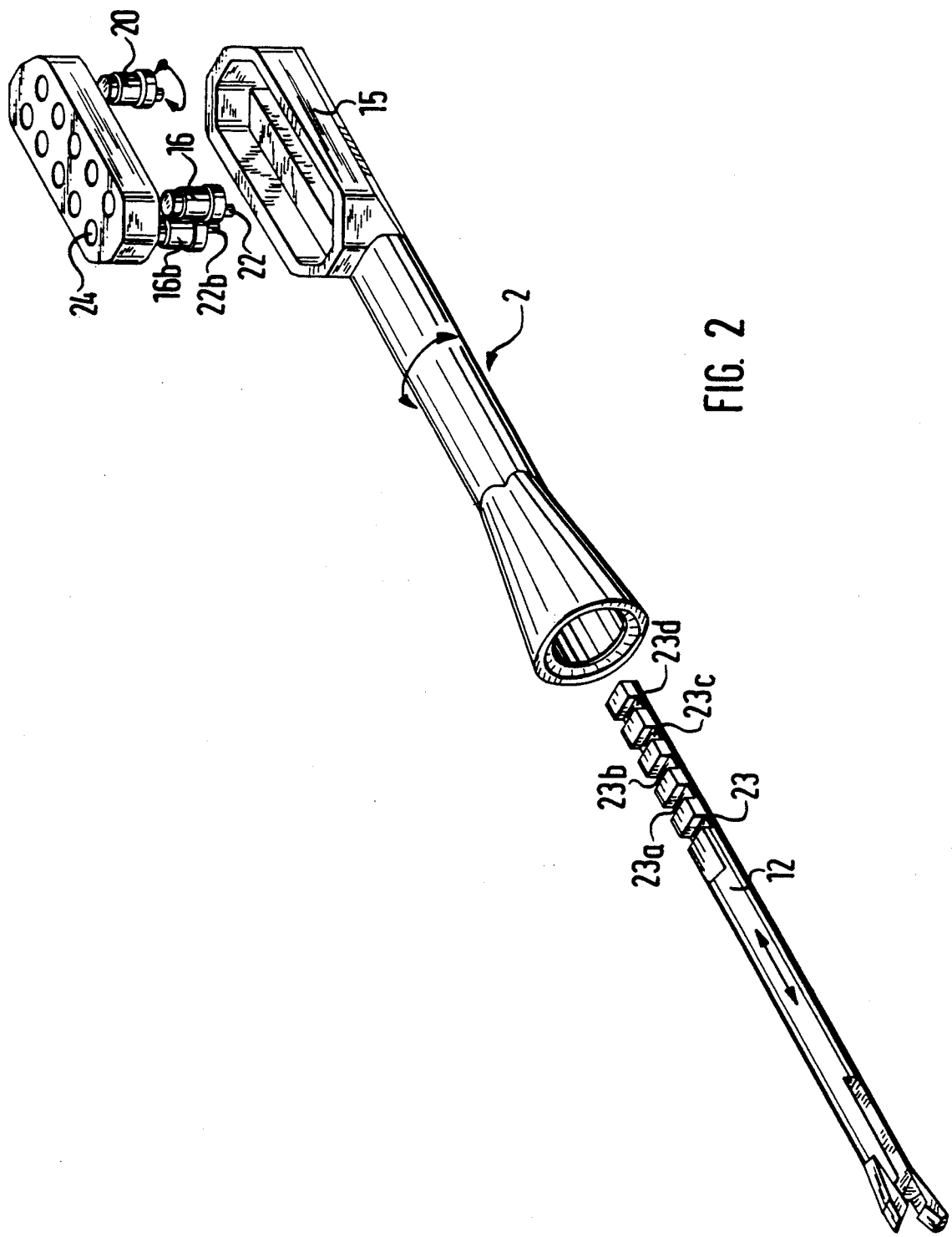
FIG. 2 shows a perspective exploded view of a brush member of the toothbrush shown in FIG. 1.

FIG. 2 clarifies the design of the brush member 2. It can be seen that the connecting rod 12 has, at its brush head end, a total of five successive, transversely running grooves 23, 23a, 23b, 23c and 23d, into which the cams 22 of the bristle holders 16 to 20 can engage. In this embodiment, the brush head 15 is constructed such that, parallel to the row of bristle holders 16 to 20, it has a further row of bristle holders of which the bristle holder 16b is shown. The bristle holder 16b and the other bristle holders in its row also engage with a respective cam 22b into these grooves 23, 23a, 23b, 23c, 23d of the connecting rod 12. As shown in FIG. 2, all bristle holders 16 to 20 and 16b are rotatably arranged in a lid 24 which can be inserted from above as an insert into the brush head 15.

Figure 3:
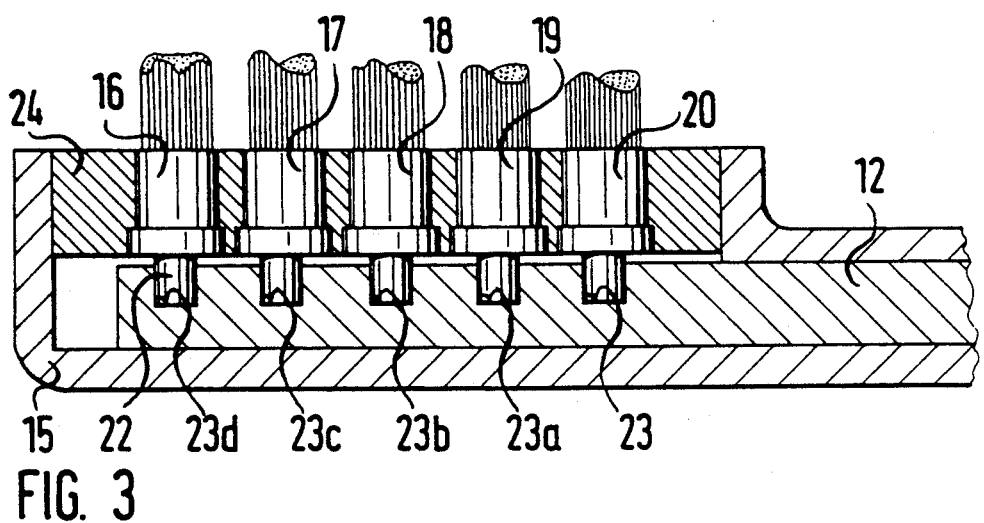
FIG. 3 shows a longitudinal section through the front region of the brush member.
Figure 4:
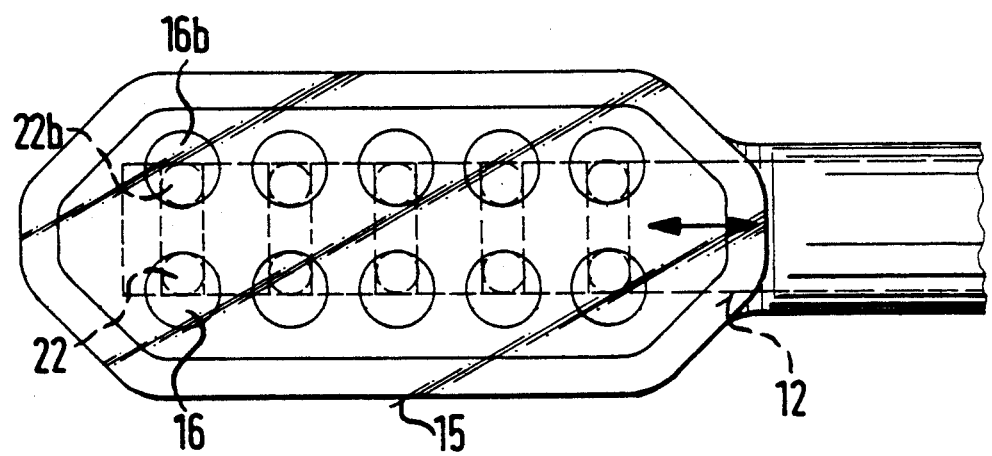
FIG. 4 shows a plan view of the front region of the brush member.

The sectional view according to FIG. 3 shows how the bristle holders 16 to 20 with their respective cams 22 engage in the respective grooves 23, 23a, 23b, 23c, 23d in the connecting rod 12. FIG. 4 shows that, in the central position of the connecting rod 12, the cams 22, 22b and, accordingly, the other cams face one another in the transverse direction of the brush head 15.

Figure 5:
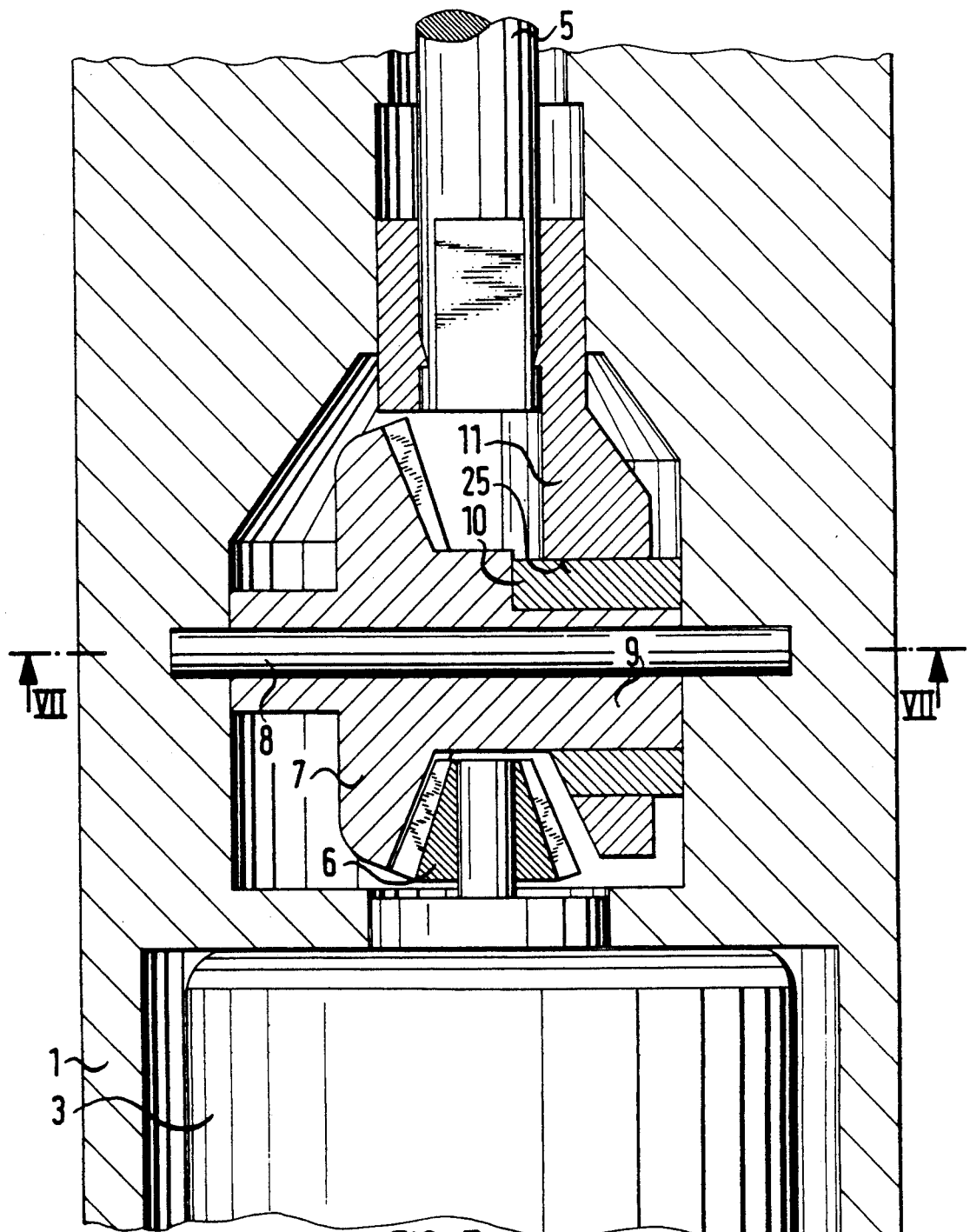
FIG. 5 shows a longitudinal section through the gearing of the toothbrush.

FIG. 5 shows, on a larger scale than FIG. 1, how the motor 3 with its bevel pinion 6 drives the bevel wheel 7. The pivot pin 8 of this bevel wheel 7 is mounted at both ends in the housing of the handle 1. It can be seen that the rocker 11 has a recess 25 in which the sliding block 10 rests. The eccentric peg 9 engages rotatably in this sliding block 10. The rocker 11 is connected non-rotatably and non-movably to the toothbrush shaft 5.

Figure 6:
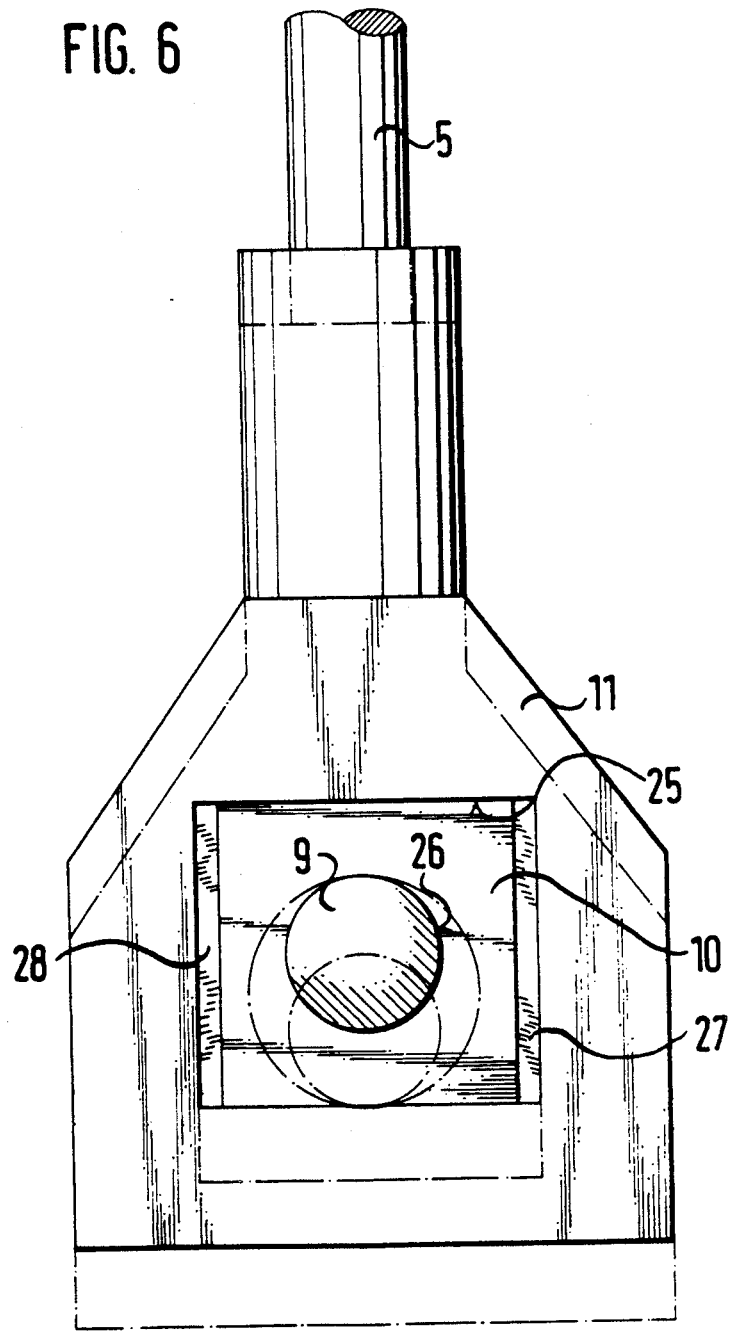
FIG. 6 shows a plan view of a rocker of the gearing with adjacent components.

FIG. 6 shows that the recess 25 in the rocker 11 rotationally engaged on the toothbrush shaft 5 is rectangular in cross section and the sliding block 10 is also rectangular accordingly. This sliding block 10 has a bore 26 into which the eccentric peg 9 engages. If the eccentric peg 9 rotates about 180° and thus assumes its lower position shown in dot dash lines, then the rocker 11 is moved downwards accordingly so that the toothbrush shaft 5 is also moved axially. As the eccentric peg 9 is located in its intermediate positions (not shown) to the side of the toothbrush shaft 5, the rocker 11 would also have to be moved laterally, but this is not possible since the toothbrush shaft 5 is laterally fixed. Instead of a sideways movement, the rocker 11 performs a rocking movement which is possible since the sliding block 10 is curved into an arc on two lateral faces 27, 28 and the toothbrush shaft 5 runs beneath the sliding block 10, as viewed in FIG. 6. A rocking moment is thus produced when the sliding block 10 in its recess 25, presses the rocker 11 to the side so that the rocker 11 rocks about the toothbrush shaft 5 and thus rotates the toothbrush shaft 5 accordingly.

Figure 7:
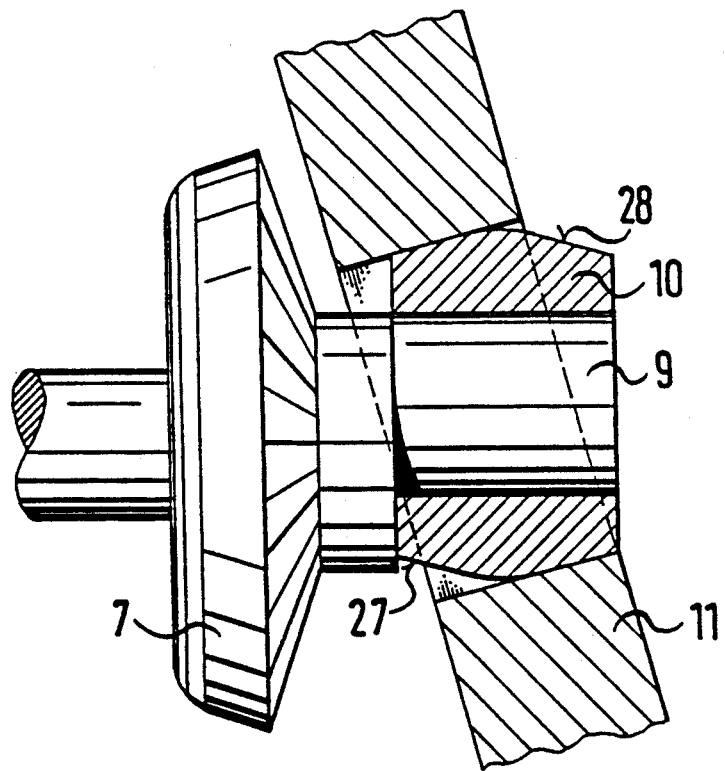
FIG. 7 shows a cross section through the toothbrush along the line VII—VII in FIG. 5.

FIG. 7 illustrates the arc-shaped lateral faces 27, 28 of the sliding block 10. The rocker 11 can thus assume the rocked position in the illustrated position of the eccentric peg 9, rotated by 90° from FIG. 6, so that it does not have to move to side.

I claim:

1. An electric toothbrush comprising:
   a handle;
   a brush member connected to the handle and including a brush head having a plurality of cylindrical and axially rotatable bristle holders, wherein each bristle holder comprises a cam eccentrically extending from a bottom portion of the bristle holder;
   a connecting rod extending along the brush member for oscillating said bristle holders, said connecting rod having a plurality of substantially transverse grooves engaged with the cams of the bristle holders; and
   driving means located within the handle and connected to the connecting rod for moving the connecting rod in a reciprocating manner along a longitudinal direction of the brush member,
   wherein the brush member is connected to the handle such that the brush member is rotatable about its longitudinal axis, and the connecting rod is fixed within the brush member such that the connecting rod is not axially rotatable independent of the brush member, said driving means producing an oscillatory rotation of the connecting rod about its longitudinal axis, in addition to moving the connecting rod in a reciprocating manner along the longitudinal direction of the brush member.

2. The electric toothbrush according to claim 1, wherein the brush head includes a first row of bristle holders and a second row of bristle holders adjacent to said first row, such that each bristle holder in the first row transversely opposes a bristle holder in the second row.

3. The electric toothbrush according to claim 2, wherein the cam of each bristle holder in the first row transversely opposes the cam of a bristle holder in the second row, and the cam of each bristle holder is oriented towards the cam of an opposing bristle holder.

4. The electric toothbrush according to claim 2, wherein each of said grooves in said connecting rod engages the cam of one bristle holder from each of the first and second rows.

5. The electric toothbrush according to claim 1, wherein the brush member is detachably connected to the handle, and the connecting rod is detachably connected to a toothbrush shaft of the driving means with a snap connection.

6. The electric toothbrush according to claim 1, wherein the driving means comprises:
   a bevel wheel axially rotatable around a pivot pin, said pivot pin located within the handle transversely to a longitudinal direction of the connecting rod;
   a motor having a rotatable bevel pinion cooperating with the bevel wheel for rotating the bevel wheel about the pivot pin;
   an eccentric peg extending from the bevel wheel in a direction parallel to the pivot pin;
   a toothbrush shaft connected to the connecting rod and oriented in a longitudinal direction of the connecting rod; and
   motion translating means for translating an axial rotation of the bevel wheel to a reciprocating movement of the toothbrush shaft along a longitudinal direction of the brush member, said motion translating means connected to the toothbrush shaft and rotatably engaging the eccentric peg of the bevel wheel.

7. The electric toothbrush according to claim 6, wherein the motion translating means includes a rocker firmly attached to the toothbrush shaft and extending to the eccentric peg of the bevel wheel, said rocker having a rectangular recess in the vicinity of the eccentric peg of the bevel wheel, and a sliding block located within said recess and having a bore which rotatably engages the eccentric peg, whereby a longitudinal movement of the sliding block causes a corresponding longitudinal movement of the rocker.

8. The electric toothbrush according to claim 7, wherein the sliding block has two opposed lateral faces each parallel to a longitudinal axis of the toothbrush shaft, said two opposed lateral faces each being arc-shaped and contacting an inner portion of the recess of the rocker, whereby a transverse movement of the sliding block causes a rotation of the rocker about a longitudinal axis of the toothbrush shaft.

9. The electric toothbrush according to claim 8, wherein a portion of the rocker containing the recess is located at a radial distance from the toothbrush shaft.

10. An electric toothbrush comprising:
    a handle;
    a brush member connected to the handle and including a brush head having a plurality of cylindrical and axially rotatable bristle holders, wherein each bristle holder comprises a cam eccentrically extending from a bottom portion of the bristle holder;
    a connecting rod extending along the brush member for oscillating said bristle holders, said connecting rod having a plurality of substantially transverse grooves engaged with the cams of the bristle holders; and
    driving means located within the handle and connected to the connecting rod for moving the connecting rod in a reciprocating manner along a longitudinal direction of the brush member,
    wherein the brush member is connected to the handle such that the brush member is not rotatable about its longitudinal axis, and the connecting rod is axially rotatable independent of the brush member, said driving means producing a reciprocal rotation of the connecting rod about its longitudinal axis in addition to moving the connecting rod in a reciprocating manner along the longitudinal direction of the brush member, whereby the connecting rod moves the bristle holders along their axis of rotation in addition to oscillating the bristle holders.

11. The electric toothbrush according to claim 10, wherein the brush head includes a first row of bristle holders and a second row of bristle holders adjacent to said first row, such that each bristle holder in the first row transversely opposes a bristle holder in the second row.

12. The electric toothbrush according to claim 11, wherein the cam of each bristle holder in the first row transversely opposes the cam of a bristle holder in the second row, and the cam of each bristle holder is oriented towards the cam of an opposing bristle holder.

13. The electric toothbrush according to claim 11, wherein each of said grooves in said connecting rod engages the cam of one bristle holder from each of the first and second rows.

14. The electric toothbrush according to claim 10, wherein the driving means comprises:
    a bevel wheel axially rotatable around a pivot pin, said pivot pin located within the handle transversely to a longitudinal direction of the connecting rod;
    a motor having a rotatable pinion cooperating with the bevel wheel for rotating the bevel wheel about the pivot pin;
    an eccentric peg extending from the bevel wheel in a direction parallel to the pivot pin;
    a toothbrush shaft connected to the connecting rod and oriented in a longitudinal direction of the connecting rod; and
    motion translating means for translating an axial rotation of the bevel wheel to a reciprocating movement of the toothbrush shaft along a longitudinal direction of the brush member, said motion translating means connected to the toothbrush shaft and rotatably engaging the eccentric peg of the bevel wheel.

15. The electric toothbrush according to claim 14, wherein the motion translating means includes a rocker firmly attached to the toothbrush shaft and extending to the eccentric peg of the bevel wheel, said rocker having a rectangular recess in the vicinity of the eccentric peg of the bevel wheel, and a sliding block located within said recess and having a bore which rotatably engages the eccentric peg, whereby a longitudinal movement of the sliding block causes a corresponding longitudinal movement of the rocker.

16. The electric toothbrush according to claim 15, wherein the sliding block has two opposed lateral faces each parallel to a longitudinal axis of the toothbrush shaft, said two opposed lateral faces each being arc-shaped and contacting an inner portion of the recess of the rocker, whereby a transverse movement of the sliding block causes a rotation of the rocker about a longitudinal axis of the toothbrush shaft.

17. The electric toothbrush according to claim 16, wherein a portion of the rocker containing the recess is located at a radial distance from the toothbrush shaft.

* * * * *